US012588686B2

(12) United States Patent　　(10) Patent No.: US 12,588,686 B2
Takayanagi et al.　　(45) Date of Patent: Mar. 31, 2026

(54) METHOD FOR PRODUCING MODIFIED PEA PROTEIN

(71) Applicants: AJINOMOTO CO., INC., Tokyo (JP); AMANO ENZYME INC., Aichi (JP)

(72) Inventors: Hiroshi Takayanagi, Kawasaki (JP); Hiroyuki Nakagoshi, Kawasaki (JP); Rikiya Ishida, Kawasaki (JP)

(73) Assignees: AJINOMOTO CO., INC., Tokyo (JP); AMANO ENZYME INC., Aichi (JP)

( * ) Notice: Subject to any disclaimer, the term of this patent is extended or adjusted under 35 U.S.C. 154(b) by 446 days.

(21) Appl. No.: 17/646,177

(22) Filed: Dec. 28, 2021

(65) Prior Publication Data

US 2022/0117259 A1　　Apr. 21, 2022

Related U.S. Application Data

(63) Continuation of application No. PCT/JP2020/026034, filed on Jul. 2, 2020.

(30) Foreign Application Priority Data

Jul. 3, 2019　(JP) ................................ 2019-124836
Mar. 25, 2020　(JP) ................................ 2020-054915

(51) Int. Cl.
*A23J 1/14*　　(2006.01)
*C07K 14/415*　　(2006.01)

(52) U.S. Cl.
CPC ............. *A23J 1/148* (2013.01); *C07K 14/415* (2013.01)

(58) Field of Classification Search
CPC ...... A23J 3/14; A23J 3/227; A23J 1/14; A23J 3/346; A23J 3/34; A23J 3/00; A23J 1/006; A23J 1/148; A23L 33/185; C07K 14/415
USPC ......... 426/634, 52, 656, 44, 46, 42, 49, 531, 426/629; 435/68.1
See application file for complete search history.

(56) References Cited

U.S. PATENT DOCUMENTS

| | | |
|---|---|---|
| 2004/0185147 A1 | 9/2004 | Hwang |
| 2005/0037125 A1† | 2/2005 | Maningat |
| 2013/0183429 A1* | 7/2013 | Samoto .................... A23L 11/65 |
| | | 426/481 |
| 2015/0257403 A1† | 9/2015 | Sanz-Valero |
| 2017/0150734 A1* | 6/2017 | Lorand ...................... A23J 3/16 |
| 2017/0318841 A1† | 11/2017 | Triantafyllou |
| 2022/0079187 A1† | 3/2022 | Stiles |
| 2022/0117260 A1* | 4/2022 | Takayanagi ................ A23J 1/14 |

FOREIGN PATENT DOCUMENTS

| | | | | | |
|---|---|---|---|---|---|
| AU | 722915 | B2 | * | 8/2000 | ............. A23L 27/21 |
| CN | 101703147 | A | | 5/2010 | |
| CN | 109068680 | A | | 12/2018 | |
| JP | 2000-050887 | A | † | 2/2000 | |
| JP | 2003511093 | A | * | 3/2003 | ................ A23J 3/34 |
| JP | 2004-283173 | A | | 10/2004 | |
| WO | WO-2011050471 | A1 | * | 5/2011 | ........... A23L 1/3053 |
| WO | WO 2015/071499 | A1 | | 5/2015 | |
| WO | WO 2017/009100 | A1 | | 1/2017 | |
| WO | WO 2018/075589 | A1 | | 4/2018 | |
| WO | WO2019/105961 | | | 6/2019 | |

OTHER PUBLICATIONS

JP-2003511093-A, Machine English translation, Mar. 25, 2003 (Year: 2003).*
International Search Report issued Sep. 15, 2020 in PCT/JP2020/026034 filed Jul. 2, 2020, 2 pages.
"Amano Enzyme: Boost Protein Solubility," Prepared Foods, Sep. 12, 2018, 2 pages.
Miroljub B. Barac, et al., "Techno-functional properties of Pea (*Pisum sativum*) protein isolates—a review," Apteff, vol. 46, 2015, 18 pages.
Extended European Search Report Issued Jun. 5, 2023 in European Application No. 20835172, 9 pages.
Yang, L. et al., Food Hydrocolloids, vol. 80, 2018, pp. 245-253.
Djoullah, A., et al., "Gelation behaviors of denatured pea albumin and globulin fractions during transglutaminase treatment," Food Hydrocolloids, vol. 77 (2018), pp. 636-645.
Yamaguchi et al., "Protein-glutaminase from Chryseobacterium proteolyticum, an enzyme that deamidates glutaminyl residues in proteins" Eur. J. Biochem. 268, 1410-1421 (2001).
Yohanna Balen Martinez et al., "L-Glutamine-, peptidyl- and protein-glutaminases: structural features and applications in the food industry" World Journal of Microbiology and Biotechnology, vol. 38, article No. 204, (2022).
Clark, K.M., Mechanistic studies of protein fractionation by precipitation with carboxymethylcellulose, 170 pages, 1988, Retrospective Theses and Dissertations. 9767.†
Singh et al., Functional & Edible Uses of Soy Protein Products, 7:14-28, 2008, Comp. Rev. in Food Sci and Food Safety.†
Suppavorasatit et al., Optimization of the Enzymatic Deamidation of Soy Protein by Protein-Glutaminase and Its Effect on the Functional Properties of the Protein, 59:11621-11628, Sep. 28, 2011, J Agric. and Food Chem.†
Amano Enzyme Offers New Food Enzyme, p. 48, Nov. 27, 2018, Food Business News.†
Guan et al., Effects of Alkaline Deamidation on the Chemical Properties of Rice Bran Protein, 23(5):697-704; 2017, Food Sci and Tech Res.†

(Continued)

*Primary Examiner* — Hong T Yoo

(74) *Attorney, Agent, or Firm* — Oblon, McClelland, Maier & Neustadt, L.L.P.

(57) ABSTRACT

Methods including performing (I) a step of adding an acid to a water dispersion of a pea ground product and collecting the precipitate, and (II) a step of conducting an enzyme reaction by adding protein deamidase, in this order or reverse order, are useful for improving the solubility of a modified pea protein.

4 Claims, 2 Drawing Sheets

(56)　　　　　　References Cited

OTHER PUBLICATIONS

Hamada et al., Preparation and Functional Properties of Enzymatically Deamidated Soy Proteins, 54(3):598-601 1989, J. Food Sci.†
Soetrisno and Holmes, Protein Yields and Characteristics from Acid and Salt Coagulations of Yellow Pea (*Pisum sativum* L. *Miranda*) Flour Extractions, 40(6):970-974, 1992, J. Agric. Food Chem.†
Yong et al., "Effect of Enzymatic Deamidation by Protein-Glutaminase on Structure and Functional Properties ofalpha-Zein", 52:7094-7100, Oct. 16, 2004, J. Agric. Food Chem.†

* cited by examiner
† cited by third party

METHOD FOR PRODUCING MODIFIED PEA PROTEIN

CROSS REFERENCES TO RELATED APPLICATIONS

This application is a continuation of International Patent Application No. PCT/JP2020/026034, filed on Jul. 2, 2020, and claims priority to Japanese Patent Application No. 2019-124836, filed on Jul. 3, 2019, and Japanese Patent Application No. 2020-054915, filed on Mar. 25, 2020, all of which are incorporated herein by reference in their entireties.

BACKGROUND OF THE INVENTION

Field of the Invention

The present invention relates to methods for producing a modified pea protein (particularly, pea protein with improved solubility); modified pea proteins (particularly, pea protein with improved solubility) obtained by said production method; and methods for improving the solubility of a pea protein.

Discussion of the Background

Pea protein has low solubility under low pH conditions. When blended in acidic foods and beverages, precipitation occurs, which tends to adversely affect the quality such as texture, appearance and the like and limit the range of use. Therefore, the development of a pea protein with increased solubility under low pH conditions is demanded.

WO 2017/009100, which is incorporated herein by reference in its entirety, discloses that the solubility at pH 6.5 was improved by adding protein glutaminase to a water dispersion of a commercially available pea protein (Pisane C9 (trade name), manufactured by Cosucra) and performing an enzymatic reaction. However, WO 2017/009100 does not describe addition of protein glutaminase in a specific step in the present invention.

SUMMARY OF THE INVENTION

Accordingly, it is one object of the present invention to provide a method for producing a modified pea protein (particularly, pea protein with improved solubility).

It is another object of the present invention to provide a modified pea protein (particularly, pea protein with improved solubility) obtained by said production method.

It is another object of the present invention to provide a method for improving the solubility of a pea protein.

These and other objects, which will become apparent during the following detailed description, have been achieved by the inventors' discovery that a pea protein with improved solubility under low pH conditions can be produced by adding protein deamidase (e.g., protein glutaminase) in a specific step of production.

Accordingly, the present invention provides the following.

(1) A method for producing a modified pea protein by using a water dispersion of a pea ground product as a starting material, comprising performing (I) a step of adding an acid and collecting the precipitate, and (II) a step of conducting an enzyme reaction by adding protein deamidase, in this order or reverse order.

(2) The production method of the above-mentioned (1), comprising (A1) a step of obtaining a water dispersion of a pea ground product by dry pulverizing the pea and mixing same with water, or wet pulverizing the pea in water, (A2) a step of adding an acid to a solution obtained by removing solid substances from the water dispersion obtained in step (A1) or the water dispersion obtained in step (A1), and collecting the precipitate, and (A3) a step of conducting an enzyme reaction by adding protein deamidase to the precipitate obtained in step (A2), or adding protein deamidase after dissolving the precipitate obtained in step (A2).

(3) The production method of the above-mentioned (1), comprising (B1) a step of obtaining a water dispersion of a pea ground product by dry pulverizing the pea and mixing same with water, or wet pulverizing the pea in water, (B2) a step of obtaining an enzymatic reaction mixture by adding protein deamidase to a solution obtained by removing solid substances from the water dispersion obtained in step (B1) or the water dispersion obtained in step (B1), and (B3) a step of adding an acid to the enzymatic reaction mixture obtained in step (B2), and collecting the precipitate.

(4) The method of any of the above-mentioned (1) to (3), wherein the protein deamidase is added in an amount of 0.1 to 1000 units per 1 g of the protein.

(5) A modified pea protein obtained by the method of any of the above-mentioned (1) to (4)].

(6) A method for improving solubility of a pea protein, comprising using a water dispersion of a pea ground product as a starting material, and performing (I) a step of adding an acid and collecting the precipitate, and (II) a step of conducting an enzyme reaction by adding protein deamidase, in this order or reverse order.

(7) The method of the above-mentioned (6), comprising (A1) a step of obtaining a water dispersion of a pea ground product by dry pulverizing the pea and mixing same with water, or wet pulverizing the pea in water, (A2) a step of adding an acid to a solution obtained by removing solid substances from the water dispersion obtained in step (A1) or the water dispersion obtained in step (A1), and collecting the precipitate, and (A3) a step of conducting an enzyme reaction by adding protein deamidase to the precipitate obtained in step (A2), or adding protein deamidase after dissolving the precipitate obtained in step (A2).

(8) The method of the above-mentioned (6), comprising (B1) a step of obtaining a water dispersion of a pea ground product by dry pulverizing the pea and mixing same with water, or wet pulverizing the pea in water, (B2) a step of obtaining an enzymatic reaction mixture by adding protein deamidase to a solution obtained by removing solid substances from the water dispersion obtained in step (B1) or the water dispersion obtained in step (B1), and (B3) a step of adding an acid to the enzymatic reaction mixture obtained in step (B2), and collecting the precipitate.

(9) The method of any of the above-mentioned (6) to (8), wherein the protein deamidase is added in an amount of 0.1 to 1000 units per 1 g of the protein.

Advantageous Effects of Invention

According to the present invention, a method for producing a modified pea protein (particularly, pea protein with improved solubility); a modified pea protein (particularly, pea protein with improved solubility) obtained by said production method; and a method for improving the solubility of a pea protein can be provided.

The modified pea protein obtained by the production method of the present invention has improved solubility under low pH conditions, and is advantageous in that it can be blended into acidic foods and beverages.

Separated pea protein powder extracted from pea is commercially available (e.g., Pisane C9 (trade name), manufactured by Cosucra). When an enzyme is added to improve the solubility of protein in a step of adding such conventional separated pea protein powder to foods and beverages to produce final products, complicated operations such as enzyme addition/reaction step, addition of control items and the like become necessary.

When final products are produced by adding the pea protein with improved solubility obtained by the production method of the present invention to foods and beverages, it is advantageous in that the addition of an enzyme is not required during the production of the final products, which simplifies the production of the final products.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
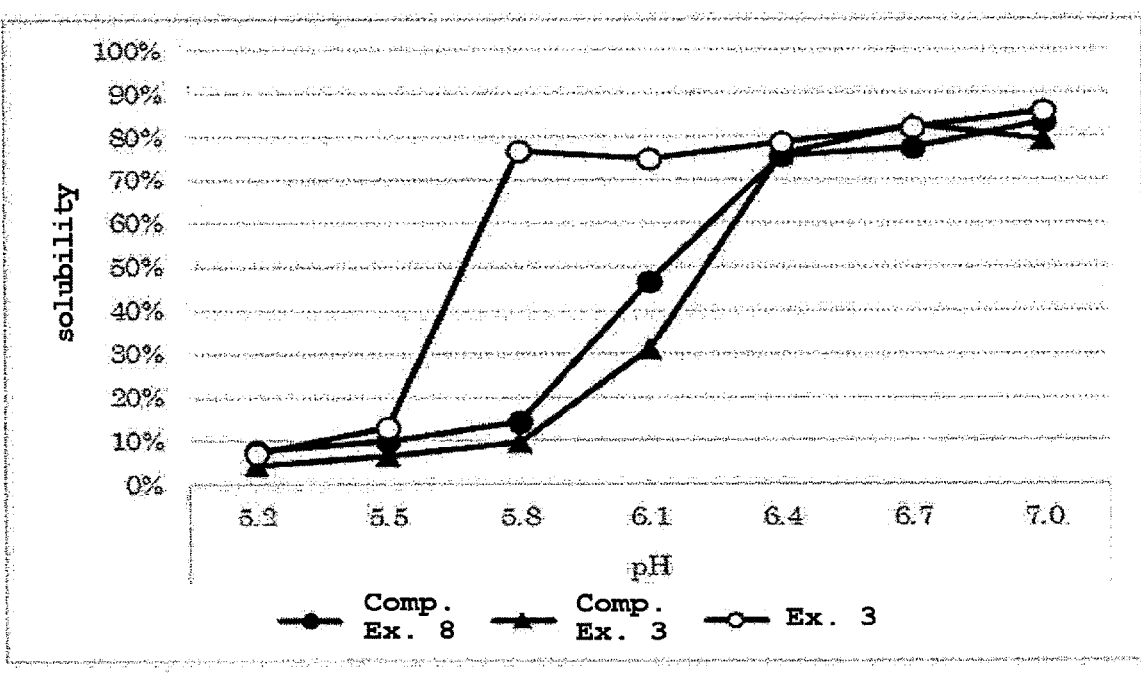
FIG. 1 shows the results of Experimental Example 3 (solubility (%) of protein in respective pH-adjusted solutions of Example 3, Comparative Example 3, Comparative Example 8).

The present invention is explained in detail in the following.

Examples of the protein deamidase in the present invention include protein glutaminase, protein asparaginase and the like.

The protein glutaminase used in the present invention has the effect of acting directly on the amide group of the protein to cause deamidation without cleavage of peptide bonds or crosslinking of the protein. The type thereof is not particularly limited as long as it has the action. As the protein glutaminase, one prepared from a culture medium of a microorganism that produces protein glutaminase can be used. The microorganism used for the preparation of protein glutaminase is not particularly limited, and microorganisms of the genus *Chryseobacterium*, the genus *Flavobacterium*, and the genus *Empedobacter* can be recited as examples. For example, as the bacteria of the genus *Chryseobacterium*,

*Chryseobacterium proteolyticum* and the like can be mentioned, as the bacteria of the genus *Flavobacterium, Flavobacterium aquatile* and the like can be mentioned, and as the bacteria of the genus *Empedobacter, Empedobacter brevis* and the like can be mentioned.

As a method for preparing protein glutaminase from a culture medium of a microorganism, known protein separation and purification methods (centrifugation, UF concentration, salting out, various chromatographys using ion exchange resin, and the like) can be used. For example, the desired enzyme can be obtained by centrifuging the culture medium to remove bacterial cells and then combining salting out, chromatography and the like. When the enzyme is recovered from the bacterial cells, the desired enzyme can be obtained by, for example, disrupting the cells by pressurization treatment, sonication, or the like, and then separating and purifying them in the same manner as described above. In addition, after recovery of the bacterial cells from the culture medium in advance by filtration, centrifugation treatment or the like, the above-mentioned series of steps (disruption, separation, purification of the bacterial cells) may be performed. The enzyme may be powderized by a drying method such as freeze-drying, drying under reduced pressure, and the like, and an appropriate excipient or drying aid may also be used at that time.

The protein glutaminase to be used in the present invention may be a commercially available product. As a specific example, a protein glutaminase commercially available under the trade name "Amano 500K protein-glutaminase" from Amano Enzyme Inc. or the like can be used.

The active unit of transglutaminase used in the present specification is measured and defined as follows.

(1) An aqueous solution (10 μl) containing protein glutaminase is added to 100 μl of 176 mM phosphate buffer (pH 6.5) containing 30 mM Z-Gln-Gly, and the mixture is incubated at 37° C. for 10 min. A 12% TCA solution (100 μl) is added to discontinue the reaction. At this time, the mixture is appropriately diluted with 20 mM phosphate buffer (pH 6.0) such that the enzyme concentration is 0.05 mg/ml.

(2) After centrifugation (12000 rpm, 4° C., 5 min), the supernatant is quantified with F-kit ammonia (manufactured by Roche) for $NH_3$. The method is as follows.

(3) To reagent II solution (F-kit accessory) (100 μl) are added 10 μl of supernatant and 190 μl of 0.1 M triethanolamine buffer (pH 8.0), and the mixture is allowed to stand at room temperature for 5 min, and 100 μl thereof is used to measure absorbance (E1) at 340 nm. To the remaining 200 μl is added 1.0 μl of Reagent III (glutamate dehydrogenase), and the mixture is allowed to stand at room temperature for 20 min, and the absorbance (E2) at 340 nm of the remaining 200 μl is measured. The concentration of ammonia in the reaction mixture is determined from the calibration curve showing the relationship between the ammonia concentration and the amount of change in the absorbance (340 nm) which is drawn using the ammonia standard solution attached to the F-kit.

(4) The protein concentration is measured using protein assay CBB (Coomassie Brilliant Blue) solution (Nacalai Tesque) at detection wavelength 595 nm. As the standard, BSA (manufactured by Pierce) is used.

(5) The activity of protein glutaminase is determined from the following formula.

$$\text{specific activity } (U/\text{mg}) = \qquad \text{numerical formula 1}$$

$$\frac{\begin{array}{c}\text{ammonia concentration of reaction} \\ \text{mixture } (\mu\text{mol}/\text{ml}) \end{array} \times \text{amount of reaction mixture (ml)} \times \text{enzyme dilution rate}}{\begin{array}{c}\text{enzyme amount (ml)} \times \\ \text{protein concentration (mg}/\text{ml}) \times \\ \text{reaction time (min)}\end{array}}$$

The protein asparaginase used in the present invention has the effect of acting directly on the amide group of the protein to cause deamidation without cleavage of peptide bonds or crosslinking of the protein. The type thereof is not particularly limited as long as it has the action. As the protein asparaginase, one prepared from a culture medium of a microorganism that produces protein asparaginase can be used. The microorganism used for the preparation of protein asparaginase is not particularly limited, and microorganisms of the genus *Luteimicrobium*, the genus *Agromyces*, the genus *Microbacterium*, and the genus *Leifsonia* can be recited as examples. Examples of the bacterium of the genus *Luteimicrobium* include *Luteimicrobium album* and the like, examples of the bacterium of the genus *Agromyces* include one type of the genus *Agromyces* (AJ111073 (NITE BP-01782)) and the like, examples of the bacterium of the genus *Microbacterium* include *Microbacterium testaceum* and the like, and examples of the bacterium of the genus *Leifsonia* include *Leifsonia xyli, Leifsonia aquatica* and the like.

The protein asparaginase used in the present invention can be produced by, for example, the method described in WO2015/133590, which is incorporated herein by reference in its entirety.

The active unit of protein asparaginase used in the present specification is measured and defined as follows.

(1) An aqueous solution (25 μl) containing protein asparaginase is added to 125 μl of 0.2 M phosphate buffer (pH 6.5) containing 30 mM Cbz-Asn-Gly, and the mixture is incubated at 37° C. for 60 min. A 12% TCA solution (150 μl) is added to discontinue the reaction.

(2) After centrifugation (15000 rpm, 4° C., 5 min), the supernatant is quantified with F-kit ammonia (manufactured by Roche) for $NH_3$. The method is as follows.

(3) To reagent II solution (F-kit accessory) (100 μl) are added μl of supernatant and 190 μl of 0.1 M triethanolamine buffer (pH 8.0), and the mixture is allowed to stand at room temperature for 5 min, and 100 μl thereof is used to measure absorbance (E1) at 340 nm. To the remaining 200 μl is added 1.0 μl of Reagent III (glutamate dehydrogenase), and the mixture is allowed to stand at room temperature for 20 min, and the absorbance (E2) at 340 nm of the remaining 200 μl is measured. The concentration of ammonia in the reaction mixture is determined from the calibration curve showing the relationship between the ammonia concentration and the amount of change in the absorbance (340 nm) which is drawn using the ammonia standard solution attached to the F-kit.

(4) The protein concentration is measured using protein assay CBB (Coomassie Brilliant Blue) solution (Nacalai Tesque) at detection wavelength 595 nm. As the standard, BSA (manufactured by Pierce) is used.

(5) The activity of protein asparaginase is determined from the following formula.

$$\text{specific activity } (U/\text{mg}) = \qquad \text{numerical formula 2}$$

$$\frac{\begin{array}{c}\text{ammonia concentration of reaction} \\ \text{mixture } (\mu\text{mol}/\text{ml}) \end{array} \times \text{amount of reaction mixture (ml)} \times \text{enzyme dilution rate}}{\begin{array}{c}\text{enzyme amount (ml)} \times \\ \text{protein concentration (mg}/\text{ml}) \times \\ \text{reaction time (min)}\end{array}}$$

The production method of the modified pea protein of the present invention includes using a water dispersion of a pea ground product as a starting material, and performing (I) a step of adding an acid and collecting the precipitate, and (II) a step of conducting an enzyme reaction by adding protein deamidase, in this order (order of step (I), step (II)) or reverse order (order of step (II), step (I)).

In the following, a production method including step (I) and step (II) in this order using a water dispersion of a pea ground product as a starting material is denoted as "the production method (A) of the modified pea protein of the present invention", and a production method including step (II) and step (I) in this order using a water dispersion of a pea ground product as a starting material is denoted as "the production method (B) of the modified pea protein of the present invention".

As the production method (A) of the modified pea protein of the present invention, a method including the following steps (A1) to (A3) is preferred.

step (A1): a step of obtaining a water dispersion of a pea ground product by dry pulverizing the pea and mixing same with water, or wet pulverizing the pea in water, step (A2): a step of adding an acid to a solution obtained by removing solid substances from the water dispersion obtained in step (A1) or the water dispersion obtained in step (A1), and collecting the precipitate, and step (A3): a step of conducting an enzyme reaction by adding protein deamidase to the precipitate obtained in step (A2), or adding protein deamidase after dissolving the precipitate obtained in step (A2).

Step (A1)

In step (A1), a water dispersion of a pea ground product is obtained by dry pulverizing the pea and mixing same with water, or wet pulverizing the pea in water.

Examples of the pea used in the present invention include yellow pea, red pea, and the like, and any kind of ripe seeds of the *Pisum sativum* can be used.

Dry pulverization can be performed by a known method, and examples thereof include impact grinding machine, pin mill, jet mill, ball mill and the like.

Water is added to the pea ground product (pea powder) obtained by dry pulverization, and the mixture is stirred to obtain a water dispersion of the pea ground product. The amount of water to be added is, for example, 60 to 1000 parts by weight per 15 parts by weight of the pea ground product. Stirring can be performed by a known method, for example, at 20° C. for 1 hr.

In addition, a water dispersion of the pea ground product can be obtained by wet pulverization.

Wet pulverization can be performed by a known method, and examples thereof include a ball mill and the like. The amount of water to be used can be appropriately selected. If necessary, water is further added to the water dispersion obtained by wet pulverization and, for example, a water dispersion of the pea ground product containing 60 to 1000 parts by weight of water per 15 parts by weight of the pea ground product can be obtained.

In the present invention, as the pea ground product, for example, one having D95, representing a cumulative volume of 95% from the small particle size side in the particle size distribution curve, of 200 μm or below can be used. The particle size can be measured by, for example, a laser diffraction/scattering type particle size distribution measuring device.

Step (A2)

In step (A2), an acid is added to a solution obtained by removing solid substances from the water dispersion obtained in step (A1) or the water dispersion obtained in step (A1), and the precipitate (separated pea protein curd) is recovered.

As a method for removing solid substances from the water dispersion obtained in step (A1), for example, centrifugation and filtration can be mentioned. Centrifugation can be performed by a known method, for example, at 20° C. (6000 g×30 min). Filtration can be performed by a known method, for example, paper filter (e.g., Whatman, 520B 1/2 FF) and the like. Centrifugation and filtration may be performed in combination. An acid is added to a solution after removal of solid substances (supernatant recovered by centrifugation, or filtrate recovered by filtration).

Examples of the acid include hydrochloric acid, sulfuric acid, phosphoric acid and the like. A precipitate is formed by adding an acid to adjust the pH to 3.0 to 6.0 (preferably pH 4.5).

Examples of the method for collecting the precipitate include centrifugation, filtration, and decantation.

Centrifugation can be performed by a known method, for example, at 20° C. (6000 g×30 min). Filtration can be performed by a known method, for example, paper filtration, or the like. Centrifugation and filtration may be performed in combination.

Step (A3)

In step (A3), an enzyme reaction is conducted by adding protein deamidase to the precipitate (separated pea protein curd) obtained in step (A2), or adding protein deamidase after dissolving the precipitate (separated pea protein curd) obtained in step (A2), whereby the modified pea protein of the present invention is obtained.

In the present invention, a powder or solution of protein deamidase is kneaded with the precipitate (paste, semi-solid), and the enzyme reaction can be conducted even in a semi-solid state. That is, water may be added to dissolve the precipitate, an alkali may be added as necessary to adjust the pH, and protein deamidase may be added to dissolve the precipitate to carry out an enzymatic reaction. Alternatively, protein deamidase may be added to the precipitate (alkali is added to adjust the pH as necessary), and they may be kneaded to carry out an enzymatic reaction.

In view of reaction efficiency/handling, it is preferable to conduct an enzyme reaction by adding protein deamidase after dissolving the precipitate and stirring the mixture. The amount of water used to dissolve the precipitate is not particularly limited as long as it can dissolve or disperse the precipitate and uniformly mix the below-mentioned alkali.

The pH adjustment (neutralization) of the precipitate or a solution of the precipitate may be performed before or after the addition of protein deamidase. Examples of the alkali used for pH adjustment include sodium hydroxide, potassium hydroxide and the like.

In the present invention, it is preferable not to perform the step of drying the precipitate obtained in the step (A2) or a solution of the precipitate before adding protein deamidase. Once the precipitate is dried, the reaction efficiency may decrease and the quality of the resulting protein may be different.

The amount of protein deamidase (e.g., protein glutaminase, protein asparaginase) to be added is preferably 0.1 to 1000 units, more preferably 1 to 100 units, particularly preferably 5 to 50 units, per 1 g of protein in the target substance (the precipitate obtained in step (A2) or solution of the precipitate). In the present specification, the "protein" of "per 1 g of the protein" is a value obtained by multiplying the amount of nitrogen contained in the target substance by the nitrogen conversion coefficient 5.7.

The enzyme reaction time after addition of protein deamidase (e.g., protein glutaminase, protein asparaginase), namely, the time from the addition of enzyme to the addition of acid is 10 min to 24 hr (preferably 1 hr). The enzyme reaction temperature varies depending on the temperature stability and optimal temperature of each enzyme. For example, it is 0 to 80° C. (preferably 50° C.) in the case of protein glutaminase, and 0 to 60° C. (preferably 35° C.) in the case of protein asparaginase. When the reaction time is less than 10 min, the effect of adding the enzyme is not sufficiently obtained, and when it exceeds 24 hr, the productivity becomes low by occupying the tank in the factory, and the like. When the reaction temperature is less than 0° C., the solution freezes and the enzymatic reaction does not proceed, and the enzyme is inactivated when it exceeds 80° C. in the case of protein glutaminase and when it exceeds 60° C. in the case of protein asparaginase. It is more preferable to stir during the enzymatic reaction, and the stirring can be performed by a known method.

In step (A3), it is preferable to include a step of heating the precipitate (separated pea protein curd) obtained in step (A2) before addition of protein deamidase.

The heating step may be performed after adding water to dissolve the precipitate obtained in step (A2) (separated pea protein curd), as long as it is before the addition of protein deamidase. The heating step may be performed before or after pH adjustment of the precipitate obtained in step (A2) (separated pea protein curd), as long as it is before the addition of protein deamidase. However, it is preferably performed after pH adjustment.

By including, before adding protein deamidase, a step of heating the precipitate obtained in step (A2), a pea protein having further improved solubility under low pH conditions can be produced (see Experimental Example 3 (Example 6) described later).

The heating temperature in the heating step is 55 to 95° C., preferably 60 to 80° C. The heating time is 1 to 120 min, preferably 5 to 60 min.

In the production method of the present invention, the modified pea protein (dried product) of the present invention can also be obtained by drying the modified pea protein of the present invention (liquid, paste, or semi-solid) obtained in step (A3).

Examples of the drying method include freeze-drying, spray drying, drum drying and the like. Drying such as freeze-drying, spray drying, drum drying and the like can be performed by a known method.

Heating before the above-mentioned drying step can deactivate the enzyme (protein deamidase). The heating temperature may be, for example, a temperature exceeding 80° C. in the case of protein glutaminase, and a temperature exceeding 60° C. in the case of protein asparaginase.

As the production method (B) of the modified pea protein of the present invention, a method including the following steps (B1) to (B3) is preferred.

step (B1): a step of obtaining a water dispersion of a pea ground product by dry pulverizing the pea and mixing same with water, or wet pulverizing the pea in water, step (B2): a step of obtaining an enzymatic reaction mixture by adding protein deamidase to a solution obtained by removing solid substances from the water dispersion obtained in step (B1) or the water dispersion obtained in step (B1), and step (B3): a step of adding an acid to the enzymatic reaction mixture obtained in step (B2), and collecting the precipitate.

Step (B1)

In step (B1), a water dispersion of a pea ground product is obtained by dry pulverizing the pea and mixing same with water, or wet pulverizing the pea in water.

Step (B1) can be performed by the same method as in the aforementioned step (A1).

Step (B2)

In step (B2), an enzymatic reaction mixture is obtained by adding protein deamidase to a solution obtained by removing solid substances from the water dispersion obtained in step (B1) or the water dispersion obtained in step (B1).

As a method for removing solid substances from the water dispersion obtained in step (B1), for example, centrifugation and filtration can be mentioned. Centrifugation can be performed by a known method, for example, at 20° C. (6000 g×30 min). Filtration can be performed by a known method, for example, paper filter (e.g., Whatman, 520B 1/2 FF) and the like. Centrifugation and filtration may be performed in combination. Protein deamidase is added to a solution after removal of solid substances (supernatant recovered by centrifugation, or filtrate recovered by filtration).

The amount of protein deamidase (e.g., protein glutaminase, protein asparaginase) to be added is preferably 0.1 to 1000 units, more preferably 1 to 100 units, particularly preferably 5 to 50 units, per 1 g of protein in the target substance (solution after removal of solid substances from the water dispersion obtained in step (B1), or the water dispersion obtained in step (B1)). In the present specification, the "protein" of "per 1 g of the protein" is a value obtained by multiplying the amount of nitrogen contained in the target substance by the nitrogen conversion coefficient 5.7.

The enzyme reaction time after addition of protein deamidase (e.g., protein glutaminase, protein asparaginase), namely, the time from the addition of enzyme to the addition of acid is 10 min to 24 hr (preferably 1 hr). The enzyme reaction temperature varies depending on the temperature stability and optimal temperature of each enzyme. For example, it is 0 to 80° C. (preferably 50° C.) in the case of protein glutaminase, and 0 to 60° C. (preferably 35° C.) in the case of protein asparaginase. When the reaction time is less than 10 min, the effect of adding the enzyme is not sufficiently obtained, and when it exceeds 24 hr, the productivity becomes low by occupying the tank in the factory, and the like. When the reaction temperature is less than 0° C., the solution freezes and the enzymatic reaction does not proceed, and the enzyme is inactivated when it exceeds 80° C. in the case of protein glutaminase and when it exceeds 60° C. in the case of protein asparaginase. It is more preferable to stir during the enzymatic reaction, and the stirring can be performed by a known method.

In the present invention, it is preferable not to perform the step of drying the pea ground product before adding protein deamidase. Once the precipitate is dried, the reaction efficiency may decrease and the quality of the resulting protein may be different.

Step (B3)

In step (B3), acid is added to the enzyme reaction mixture obtained step (B2), and the precipitate (separated pea protein curd) is recovered.

Examples of the acid include hydrochloric acid, sulfuric acid, phosphoric acid and the like. A precipitate is formed by adding an acid to adjust the pH to 3.0 to 6.0 (preferably pH 4.5).

Examples of the method for collecting the precipitate include centrifugation, filtration, and decantation.

Centrifugation can be performed by a known method, for example, at 20° C. (6000 g×30 min). Filtration can be performed by a known method, for example, paper filtration, or the like. Centrifugation and filtration may be performed in combination.

Neutralization of the precipitate is preferably performed after dissolving the precipitate, in view of handling. The amount of water used to dissolve the precipitate is not particularly limited as long as it can dissolve or disperse the precipitate and uniformly mix the below-mentioned alkali.

Examples of the alkali to be used for adjusting pH (neutralization) of the precipitate or the solution of the precipitate include sodium hydroxide, potassium hydroxide and the like.

In the production method of the present invention, the modified pea protein (dried product) of the present invention can also be obtained by drying the modified pea protein of the present invention (liquid, paste, or semi-solid) obtained in step (B3).

Examples of the drying method include freeze-drying, spray drying, drum drying and the like. Drying such as freeze-drying, spray drying, drum drying and the like can be performed by a known method.

Heating before the above-mentioned drying step can deactivate the enzyme (protein deamidase). The heating temperature may be any temperature exceeding 80° C. in the case of protein glutaminase, and 60° C. in the case of protein asparaginase.

When an enzyme is added to improve the solubility of protein in a step of adding conventional separated pea protein powder to foods and beverages to produce final products, the final products manufactured without undergoing a deactivation step such as heating and the like after enzyme addition are obliged to indicate the enzyme in the raw material labeling, which in turn develops disadvantages such as change of packaging materials, reduction of acceptability for distribution and consumers, and the like.

In the production method of the present invention, the pea protein with improved solubility which is obtained via the above-mentioned drying step is advantageous in that there is no need for further deactivation step such as heating and the like when manufacturing the final product or description of the enzyme in the final product label, as long as sufficient heating capable of deactivating the enzyme can be performed between the enzyme addition step and the drying step.

The modified pea protein of the present invention can be obtained by the above-mentioned production method of the present invention. The term "modified" means that the properties of the pea protein such as solubility and the like have changed by the enzymatic reaction.

The modified pea protein of the present invention has improved solubility under low pH conditions.

The modified pea protein of the present invention has improved solubility at pH 7 or below (preferably pH 6.4 or below, particularly preferably pH 6.1 or below).

The modified pea protein of the present invention has improved solubility particularly within the range of pH 5.2 to pH 7.0 (preferably pH 5.2 to pH 6.4, particularly preferably pH 5.5 to pH 6.1).

The modified pea protein of the present invention can be safely ingested by humans and non-human animals (e.g., mammals and birds such as livestock, poultry, laboratory animals and the like) directly or by adding to food (feed).

The intake amount of the modified pea protein of the present invention is not particularly limited, and may be appropriately selected according to the protein intake of general food (feed).

In the present specification, food is a concept that broadly includes foods that can be ingested orally (excluding pharmaceutical products), and includes not only so-called "food" but also beverages, health supplement, food with health claims (e.g., food for specified health uses, food with functional claims, food with nutrient function claims), supplement, and the like.

The modified pea protein of the present invention is advantageous in that it is less likely to precipitate than the conventional pea protein when blended in acidic foods and beverages.

The present invention also relates to a method for improving solubility of a pea protein.

The method for improving solubility of pea protein of the present invention includes using a water dispersion of a pea ground product as a starting material, and performing (I) a step of adding an acid and collecting the precipitate, and (II) a step of conducting an enzyme reaction by adding protein deamidase, in this order (order of step (I), step (II)) or reverse order (order of step (II), step (I)).

In the following, a method including step (I) and step (II) in this order using a water dispersion of a pea ground product as a starting material is denoted as "the method (A) for improving the solubility of a pea protein of the present invention", and a method including step (II) and step (I) in this order using a water dispersion of a pea ground product as a starting material is denoted as "the method (B) for improving the solubility of a pea protein of the present invention".

As the method (A) for improving the solubility of a pea protein of the present invention, a method including the following steps (A1) to (A3) is preferred.

step (A1): a step of obtaining a water dispersion of a pea ground product by dry pulverizing the pea and mixing same with water, or wet pulverizing the pea in water, step (A2): a step of adding an acid to a solution obtained by removing solid substances from the water dispersion obtained in step (A1) or the water dispersion obtained in step (A1), and collecting the precipitate, and step (A3): a step of conducting an enzyme reaction by adding protein deamidase to the precipitate obtained in step (A2), or adding protein deamidase after dissolving the precipitate obtained in step (A2).

As the method (B) for improving the solubility of a pea protein of the present invention, a method including the following steps (B1) to (B3) is preferred.

step (B1): a step of obtaining a water dispersion of a pea ground product by dry pulverizing the pea and mixing same with water, or wet pulverizing the pea in water, step (B2): a step of obtaining an enzymatic reaction mixture by adding protein deamidase to a solution obtained by removing solid substances from the water dispersion obtained in step (B1) or the water dispersion obtained in step (B1), and step (B3): a step of adding an acid to the enzymatic reaction mixture obtained in step (B2), and collecting the precipitate.

The steps (A1) to (A3), (B1) to (B3) of the method for improving the solubility of the pea protein of the present invention can be performed similarly to the steps (A1) to (A3), (B1) to (B3) of the aforementioned production method of the modified pea protein of the present invention. In addition, the method for improving the solubility of the pea protein of the present invention may include the drying step explained for the production method.

The method of the present invention improves the solubility of pea protein under low pH conditions.

The solubility of pea protein is improved at pH 7 or below (preferably pH 6.4 or below, particularly preferably pH 6.1 or below) by the method of the present invention.

The solubility of pea protein is improved particularly within the range of pH 5.2 to pH 7.0 (preferably pH 5.2 to pH 6.4, further preferably pH 5.5 to pH 6.1) by the method of the present invention.

In the present invention, the solubility can be measured, for example, by the method described in the below-mentioned Experimental Example 1.

Other features of the invention will become apparent in the course of the following descriptions of exemplary embodiments which are given for illustration of the invention and are not intended to be limiting thereof.

EXAMPLES

In the following Examples, Amano 500K protein-glutaminase (trade name) (Amano Enzyme Inc.) was used as protein glutaminase.

Example 1

Water (85 parts by weight) was added to 15 parts by weight of yellow pea powder obtained by dry pulverization of yellow peas (powder with D95 of 149 μm or less as the standard particle size measured by a laser diffraction/scattering type particle size distribution measuring device), and the mixture was stirred at 20° C. for 1 hr, and centrifuged at 20° C. (6000 g×30 min). The supernatant was collected and filtered through a paper filter (Whatman, 520B 1/2 FF) to obtain a pea solution. To the obtained pea solution was added hydrochloric acid to adjust the pH to 4.5, and the mixture was stirred at 20° C. for 30 min and centrifuged at 20° C. (6000 g×30 min). The precipitate was collected to obtain a separated pea protein curd. Water (3 parts by weight) was added to 1 part by weight of the obtained curd to disperse the curd. Sodium hydroxide was added to adjust the solution pH to 7.0, and the curd was dissolved to obtain a separated pea protein solution. To the obtained separated pea protein solution was added 10 units of protein glutaminase per 1 g of protein, and the mixture was stirred at 50° C. for 1 hr. The solution was frozen and lyophilized to obtain a dried separated pea protein of Example 1.

Comparative Example 1

By the same method as in Example 1 except that "To the obtained separated pea protein solution was added 10 units of protein glutaminase per 1 g of protein, and the mixture was stirred at 50° C. for 1 hr" in Example 1 was changed to "The obtained pea protein solution was stirred at 50° C. for 1 hr (without addition of protein glutaminase)", a dried separated pea protein of Comparative Example 1 was obtained.

Experimental Example 1

To 2 parts by weight of each of the dried separated pea proteins obtained in Example 1 and Comparative Example 1 was added 98 parts by weight of water, and hydrochloric acid and sodium hydroxide were added to adjust the pH to 5.5 and 7.0. The mixtures were stirred at 20° C. for 2 hr to obtain respective separated pea protein dispersions with adjusted pH.

The obtained respective separated pea protein dispersions with adjusted pH were centrifuged (20000 g×10 min) at 20° C. and the supernatants (respective pH-adjusted solutions) were collected. The nitrogen concentration thereof was measured by the Kjeldahl method, and the solubility of the protein was determined by the following formula. The results are shown in Table 1.

Protein solubility (%)=amount of nitrogen contained in supernatant/amount of nitrogen contained in entire pH-adjusted dispersion sample

TABLE 1

| solubility of freeze-dried pea protein | | |
|---|---|---|
| | solubility (%) | |
| sample | Example 1 | Comparative Example 1 |
| amount of protein glutaminase added (units/protein) | 10 | 0 |
| pH          7.0 | 82 | 70 |
| 5.5 | 12 | 8 |

Example 2

Water (85 parts by weight) was added to 15 parts by weight of yellow pea powder obtained by dry pulverization of yellow peas (powder with D95 of 149 μm or less as the standard particle size measured by a laser diffraction/scattering type particle size distribution measuring device), and the mixture was stirred at 20° C. for 1 hr, and centrifuged at 20° C. (6000 g×30 min). The supernatant was collected and filtered through a paper filter (Whatman, 520B 1/2 FF) to obtain a pea solution. To the obtained pea solution was added hydrochloric acid to adjust the pH to 4.5, and the mixture was stirred at 20° C. for 30 min and centrifuged at 20° C. (6000 g×30 min). The precipitate was collected to obtain a separated pea protein curd. Water (3 parts by weight) was added to 1 part by weight of the obtained curd to disperse the curd. Sodium hydroxide was added to adjust the solution pH to 7.0, and the curd was dissolved to obtain a separated pea protein solution. To the obtained separated pea protein solution was added 20 units of protein glutaminase per 1 g of protein, and the mixture was stirred at 50° C. for 1 hr. The solution was spray dried to obtain a dried separated pea protein of Example 2.

Comparative Example 2

By the same method as in Example 2 except that "To the obtained separated pea protein solution was added 20 units of protein glutaminase per 1 g of protein, and the mixture was stirred at 50° C. for 1 hr" in Example 2 was changed to "The obtained separated pea protein solution was stirred at 50° C. for 1 hr (without addition of protein glutaminase)", a dried separated pea protein of Comparative Example 2 was obtained.

Experimental Example 2

To 2 parts by weight of each of the dried separated pea proteins obtained in Example 2 and Comparative Example 2 was added 98 parts by weight of water, and hydrochloric acid and sodium hydroxide were added to adjust the pH to 5.2, 5.5, 5.8 and 7.0. The mixtures were stirred at 20° C. for 2 hr to obtain respective separated pea protein dispersions with adjusted pH.

The respective separated pea protein dispersions with adjusted pH were centrifuged (20000 g×10 min) at 20° C. and the supernatants (respective pH-adjusted solutions) were collected. The nitrogen concentration thereof was measured by the Kjeldahl method, and the solubility of the protein was determined by the above-mentioned formula. The results are shown in Table 2.

TABLE 2

| solubility of spray dried pea protein | | |
|---|---|---|
| | solubility (%) | |
| sample | Example 2 | Comparative Example 2 |
| amount of protein glutaminase added (units/protein) | 20 | 0 |
| pH          7.0 | 80 | 71 |
| 5.8 | 76 | 17 |
| 5.5 | 17 | 9 |
| 5.2 | 8 | 8 |

Example 3

Water (85 parts by weight) was added to 15 parts by weight of yellow pea powder obtained by dry pulverization of yellow peas (powder with D95 of 50 μm or less as the particle size measured by a laser diffraction/scattering type particle size distribution measuring device), 21 units of protein glutaminase was added per 1 g of protein, and the mixture was stirred at 50° C. for 1 hr, and centrifuged at 20° C. (6000 g×30 min). The supernatant was collected and filtered through a paper filter (Whatman, 520B 1/2 FF) to obtain a pea solution. To the obtained pea solution was added hydrochloric acid to adjust the pH to 4.5, and the mixture was stirred at 20° C. for 30 min and centrifuged at 20° C. (6000 g×30 min). The precipitate was collected to obtain a separated pea protein curd. Water (3 parts by weight) was added to 1 part by weight of the obtained curd to disperse the curd. Sodium hydroxide was added to adjust the solution pH to 7.0, and the curd was dissolved to obtain a separated pea protein solution. The solution was frozen and lyophilized to obtain a dried separated pea protein of Example 3.

Comparative Example 3

By the same method as in Example 3 except that "Water (85 parts by weight) was added to 15 parts by weight of yellow pea powder obtained by dry pulverization of yellow peas (powder with D95 of 50 μm or less as the particle size measured by a laser diffraction/scattering type particle size distribution measuring device), 21 units of protein glutaminase was added per 1 g of protein, and the mixture was stirred at 50° C. for 1 hr" in Example 3 was changed to "Water (85 parts by weight) was added to 15 parts by weight of yellow pea powder obtained by dry pulverization of yellow peas (powder with D95 of 50 μm or less as the particle size measured by a laser diffraction/scattering type particle size distribution measuring device), and the mixture was stirred at 50° C. for 1 hr (without addition of protein glutaminase)", a dried separated pea protein of Comparative Example 3 was obtained.

Example 4

Water (85 parts by weight) was added to 15 parts by weight of yellow pea powder obtained by dry pulverization of yellow peas (powder with D95 of 50 μm or less as the particle size measured by a laser diffraction/scattering type particle size distribution measuring device), and the mixture was stirred at 20° C. for 1 hr, and centrifuged at 20° C. (6000 g×30 min). The supernatant was collected and filtered through a paper filter (Whatman, 520B 1/2 FF) to obtain a pea solution. To the obtained pea solution was added 24 units of protein glutaminase per 1 g of protein, and the mixture was stirred at 50° C. for 1 hr. Hydrochloric acid was added to this solution to adjust the pH to 4.5, and the mixture was stirred at 20° C. for 30 min and centrifuged at 20° C. (6000 g×30 min). The precipitate was collected to obtain a separated pea protein curd. Water (3 parts by weight) was added to 1 part by weight of the obtained curd to disperse the curd. Sodium hydroxide was added to adjust the solution pH to 7.0, and the curd was dissolved to obtain a separated pea protein solution. The solution was frozen and lyophilized to obtain a dried separated pea protein of Example 4.

Comparative Example 4

By the same method as in Example 4 except that "To the obtained pea solution was added 24 units of protein glutaminase per 1 g of protein, and the mixture was stirred at 50° C. for 1 hr" in Example 4 was changed to "The obtained pea solution was stirred at 50° C. for 1 hr (without addition of protein glutaminase)", a dried separated pea protein of Comparative Example 4 was obtained.

Example 5

Water (85 parts by weight) was added to 15 parts by weight of yellow pea powder obtained by dry pulverization of yellow peas (powder with D95 of 50 μm or less as the particle size measured by a laser diffraction/scattering type particle size distribution measuring device), and the mixture was stirred at 20° C. for 1 hr, and centrifuged at 20° C. (6000 g×30 min). The supernatant was collected and filtered through a paper filter (Whatman, 520B 1/2 FF) to obtain a pea solution. To the obtained pea solution was added hydrochloric acid to adjust the pH to 4.5, and the mixture was stirred at 20° C. for 30 min and centrifuged at 20° C. (6000 g×30 min). The precipitate was collected to obtain a separated pea protein curd. Water (3 parts by weight) was added to 1 part by weight of the obtained curd to disperse the curd. Sodium hydroxide was added to adjust the solution pH to 7.0, and the curd was dissolved to obtain a separated pea protein solution. To the obtained separated pea protein solution was added 17 units of protein glutaminase per 1 g of protein, and the mixture was stirred at 50° C. for 1 hr. The solution was frozen and lyophilized to obtain a dried separated pea protein of Example 5.

Comparative Example 5

By the same method as in Example 5 except that "To the obtained separated pea protein solution was added 17 units of protein glutaminase per 1 g of protein, and the mixture was stirred at 50° C. for 1 hr" in Example 5 was changed to "The obtained separated pea protein solution was stirred at 50° C. for 1 hr (without addition of protein glutaminase)", a dried separated pea protein of Comparative Example 5 was obtained.

Example 6

By the same method as in Example 5 except that "To the obtained separated pea protein solution was added 17 units of protein glutaminase per 1 g of protein, and the mixture was stirred at 50° C. for 1 hr" in Example 5 was changed to "The obtained separated pea protein solution was stirred at 75° C. for 15 min, cooled to 50° C. with ice water, 17 units of protein glutaminase was added per 1 g of protein, and the mixture was stirred at 50° C. for 1 hr", a dried separated pea protein of Example 6 was obtained.

Comparative Example 6

By the same method as in Example 5 except that "To the obtained separated pea protein solution was added 17 units of protein glutaminase per 1 g of protein, and the mixture was stirred at 50° C. for 1 hr" in Example 5 was changed to "The obtained separated pea protein solution was stirred at 75° C. for 15 min, and cooled with ice water", a dried separated pea protein of Comparative Example 6 was obtained.

Comparative Example 7

By the same method as in Example 5 except that "To the obtained separated pea protein solution was added 17 units of protein glutaminase per 1 g of protein, and the mixture was stirred at 50° C. for 1 hr" in Example 5 was changed to "The obtained separated pea protein solution was stirred at 75° C. for 15 min, cooled to 50° C. with ice water, and the mixture was stirred at 50° C. for 1 hr (without addition of protein glutaminase)", a dried separated pea protein of Comparative Example 7 was obtained.

Comparative Example 8

By the same method as in Example 5 except that "To the obtained separated pea protein solution was added 17 units of protein glutaminase per 1 g of protein, and the mixture was stirred at 50° C. for 1 hr. The solution was frozen and lyophilized to obtain a dried separated pea protein of Example 5" in Example 5 was changed to "The obtained separated pea protein solution was frozen and lyophilized to obtain a dried separated pea protein of Example 8", a dried separated pea protein of Comparative Example 8 was obtained.

Experimental Example 3

To 2 parts by weight of each of the dried separated pea proteins obtained in Examples 3 to 6 and Comparative Examples 3 to 8 was added 98 parts by weight of water, and hydrochloric acid and sodium hydroxide were added to adjust the pH to 5.2, 5.5, 5.8, 6.1, 6.4, 6.7 and 7.0. The mixtures were stirred at 20° C. for 2 hr to obtain respective separated pea protein dispersions with adjusted pH.

The respective separated pea protein dispersions with adjusted pH were centrifuged (15000 g×10 min) at 20° C. and the supernatants (respective pH-adjusted solutions) were collected. The nitrogen concentration thereof was measured by the Kjeldahl method, and the solubility of the protein was determined by the above-mentioned formula.

Figure 2:
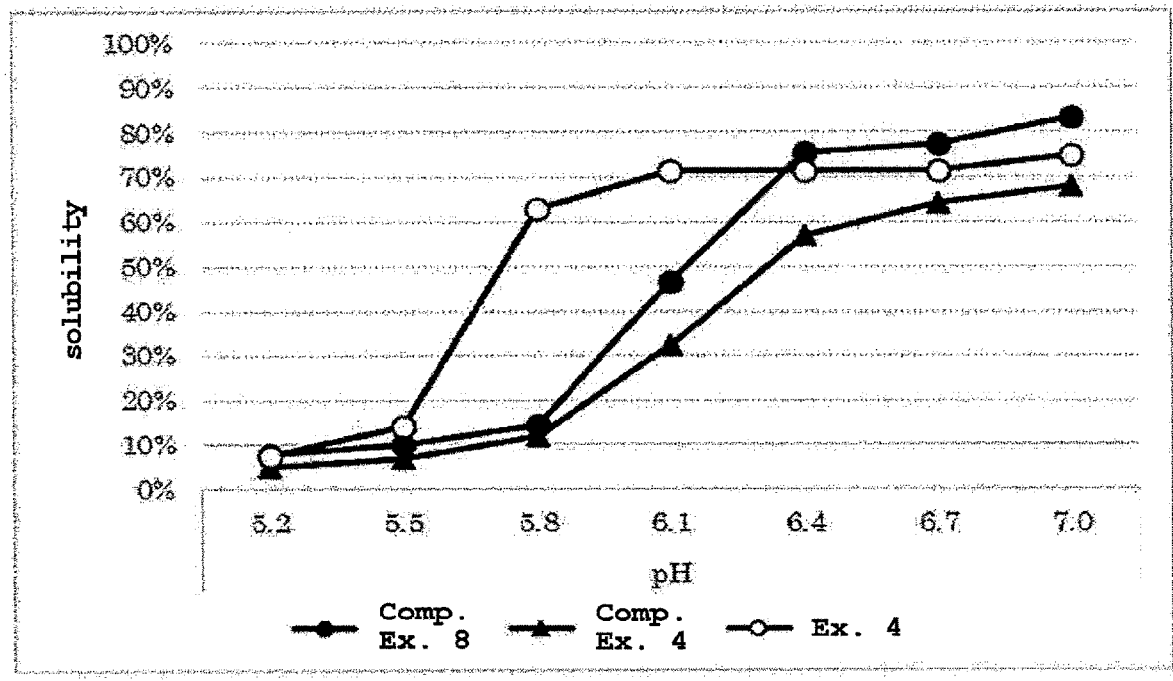
FIG. 2 shows the results of Experimental Example 3 (solubility (%) of protein in respective pH-adjusted solutions of Example 4, Comparative Example 4, Comparative Example 8).
Figure 3:
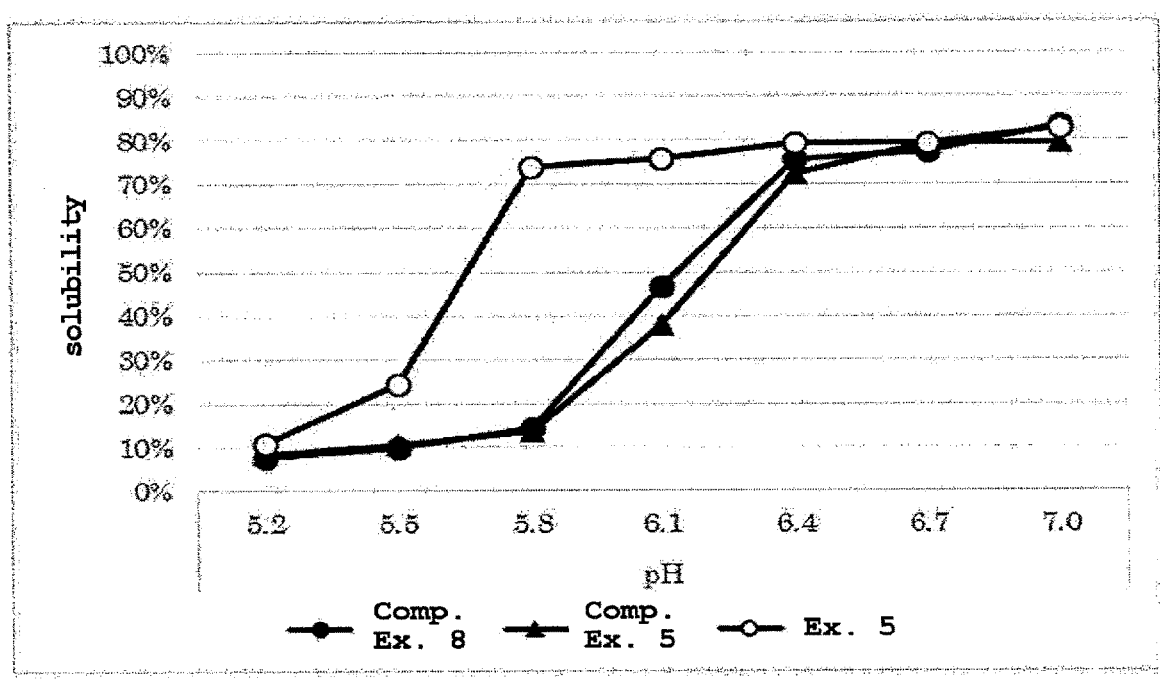
FIG. 3 shows the results of Experimental Example 3 (solubility (%) of protein in respective pH-adjusted solutions of Example 5, Comparative Example 5, Comparative Example 8).
Figure 4:
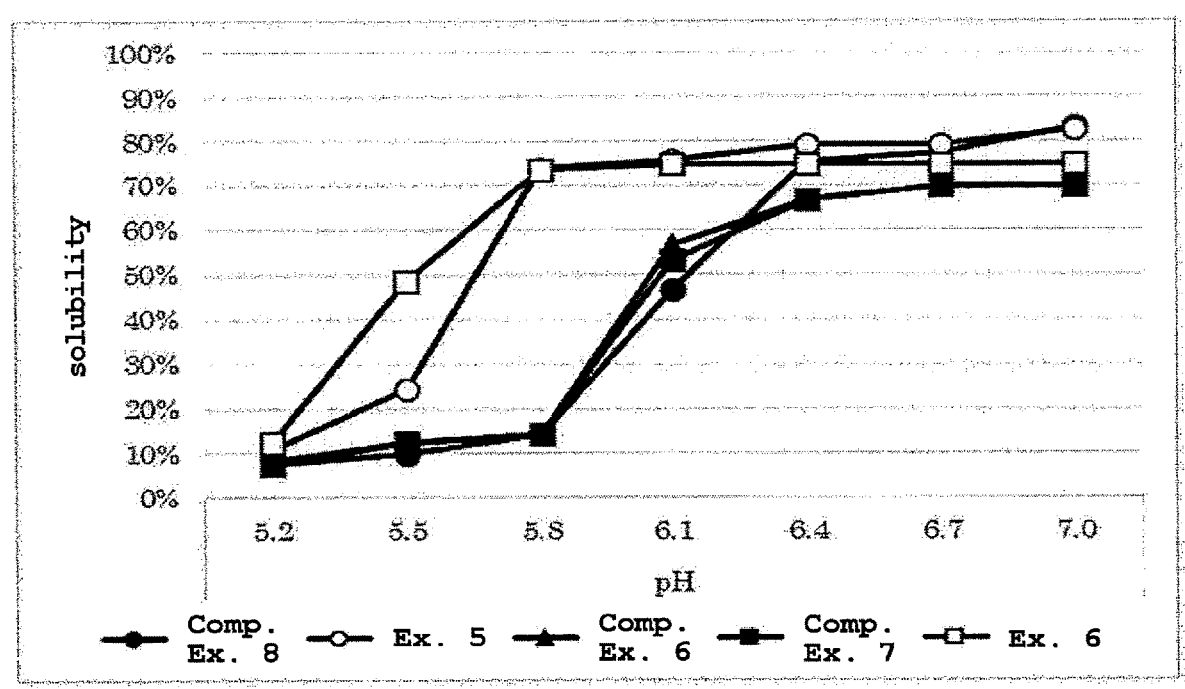
FIG. 4 shows the results of Experimental Example 3 (solubility (%) of protein in respective pH-adjusted solutions of Example 5, Example 6, Comparative Example 6, Comparative Example 7, Comparative Example 8).

The results are shown in FIGS. 1 to 4.

INDUSTRIAL APPLICABILITY

According to the present invention, a method for producing a modified pea protein (particularly, pea protein with improved solubility) and the like can be provided.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for producing a modified pea protein, comprising:

(A1) dry pulverizing a pea into a pea ground product and mixing the pea ground product with water, or wet pulverizing a pea in water, to obtain a water dispersion of a ground pea product, (A2) adding an acid to (i) a solution obtained by removing solid substances from the water dispersion of a ground pea product obtained in step (A1) or (ii) the water dispersion obtained in step (A1), to obtain a precipitate and collecting the precipitate, and (A3) conducting an enzyme reaction by adding protein deamidase to the precipitate obtained in step (A2), or adding protein deamidase after dissolving the precipitate obtained in step (A2), to obtain the modified pea protein, wherein the protein deamidase is protein glutaminase or protein asparaginase, wherein the protein deamidase is added in an amount of 1 to 1000 units per 1 g of the protein, and wherein the protein glutaminase or the protein asparaginase alone is used as the enzyme.

2. A method for producing a modified pea protein, comprising:

(B1) dry pulverizing a pea into a pea ground product and mixing the pea ground product with water, or wet pulverizing a pea in water, to obtain a water dispersion of a pea ground product, (B2) adding protein deamidase to (i) a solution obtained by removing solid substances from the water dispersion of a ground pea product obtained in step (B1) or (ii) the water dispersion obtained in step (B1), to obtain an enzymatic reaction mixture, and (B3) adding an acid to the enzymatic reaction mixture obtained in step (B2), to obtain a precipitate, and collecting the precipitate, which contains the modified pea protein, wherein the protein deamidase is protein glutaminase or protein asparaginase, wherein the protein deamidase is added in an amount of 1 to 1000 units per 1 g of the protein, and wherein the protein glutaminase or the protein asparaginase alone is used as the enzyme.

3. A method for improving solubility of a pea protein, comprising:

(A1) dry pulverizing a pea into a pea ground product and mixing the pea ground product with water, or wet pulverizing a pea in water, (A2) adding an acid to (i) a solution obtained by removing solid substances from the water dispersion of a pea ground product obtained in step (A1) or (ii) the water dispersion obtained in step (A1), to obtain a precipitate, and collecting the precipitate, and (A3) conducting an enzyme reaction by adding protein deamidase to the precipitate obtained in step (A2), or adding protein deamidase after dissolving the precipitate obtained in step (A2), to obtain the modified pea protein with improved solubility, wherein the protein deamidase is protein glutaminase or protein asparaginase, wherein the protein deamidase is added in an amount of 1 to 1000 units per 1 g of the protein, and wherein the protein glutaminase or the protein asparaginase alone is used as the enzyme.

4. A method for improving solubility of a pea protein, comprising:

(B1) dry pulverizing a pea into a pea ground product and mixing the pea ground product with water, or wet pulverizing a pea in water, to obtain a water dispersion of a pea ground product, (B2) adding protein deamidase to (i) a solution obtained by removing solid substances from the water dispersion of a pea ground product obtained in step (B1) or (ii) the water dispersion obtained in step (B1), to obtain an enzymatic reaction mixture, and (B3) adding an acid to the enzymatic reaction mixture obtained in step (B2), to obtain a precipitate, and collecting the precipitate, which contains the modified pea protein with improved solubility, wherein the protein deamidase is protein glutaminase or protein asparaginase, wherein the protein deamidase is added in an amount of 1 to 1000 units per 1 g of the protein, and wherein the protein glutaminase or the protein asparaginase alone is used as the enzyme.

* * * * *